(12) United States Patent
Alexander et al.

(10) Patent No.: US 7,515,964 B1
(45) Date of Patent: Apr. 7, 2009

(54) MULTI-DIRECTIONAL BORE CONFIGURATION HEADER

(75) Inventors: William Alexander, Castaic, CA (US); Christopher Fleck, Canyon Country, CA (US)

(73) Assignee: Pacesetter, Inc., Sylmar, CA (US)

( * ) Notice: Subject to any disclaimer, the term of this patent is extended or adjusted under 35 U.S.C. 154(b) by 228 days.

(21) Appl. No.: 11/239,537

(22) Filed: Sep. 28, 2005

(51) Int. Cl.
*A61N 1/02* (2006.01)
(52) U.S. Cl. .............................. 607/38; 607/36; 607/37
(58) Field of Classification Search ................. 439/909; 607/36–38
See application file for complete search history.

(56) References Cited

U.S. PATENT DOCUMENTS

| | | | |
|---|---|---|---|
| RE31,990 E | 9/1985 | Sluetz et al. ............. 128/419 P |
| 4,934,366 A | 6/1990 | Truex et al. ............. 128/419 P |
| 5,336,246 A * | 8/1994 | Dantanarayana ............. 607/37 |
| 5,383,913 A * | 1/1995 | Schiff ........................... 607/38 |
| 5,383,914 A | 1/1995 | O'Phelan ..................... 607/38 |
| 5,388,578 A | 2/1995 | Yomtov et al. ............. 128/642 |
| 5,843,141 A | 12/1998 | Bischoff et al. ............... 607/37 |
| 6,198,969 B1 | 3/2001 | Kuzma ......................... 607/37 |
| 6,755,694 B2 | 6/2004 | Ries et al. .................... 439/668 |

FOREIGN PATENT DOCUMENTS

GB 2127629 * 4/1984

* cited by examiner

*Primary Examiner*—Carl H Layno
*Assistant Examiner*—Yun Haeng Lee (57) ABSTRACT

An implantable medical device includes a sealed casing enclosing electronic circuitry and a plurality of electrical terminals connected to the electronic circuitry and projecting out of a mounting surface. A header has an undersurface for mounting engagement on the mounting surface of the casing and first and second oppositely directed elongated receptacles, the first receptacle being positioned proximate the electrical terminals. The header also includes at least one conductive connector block having a bore aligned with each of the first and second receptacles for receiving a proximal end portion of a lead extending through the elongated receptacle and carrying at least one electrical terminal and a wire electrically connects each of the connector blocks with an associated electrical terminal, at least the wire from the connector block associated with the first receptacle being of minimal length because of its close proximity to the plurality of electrical terminals.

15 Claims, 8 Drawing Sheets

MULTI-DIRECTIONAL BORE CONFIGURATION HEADER

FIELD OF THE INVENTION

The present invention relates to an electrical connector used with an implantable medical device, such as a pacemaker, for connecting implantable electrical leads to the electrical circuits within a hermetically sealed housing of the medical device, and more particularly, to an improved configuration which provides many benefits for both the construction and implantation of the medical device.

BACKGROUND OF THE INVENTION

Modern pacemakers monitor the activity of a heart and provide a stimulation pulse in the absence of normal heart activity. Such devices are relatively small, light-weight and implantable. In order to sense and stimulate the heart, however, such pacemakers must be used with a pacemaker lead— an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable, connection. Those skilled in the pacemaker art have long sought for a simple, yet reliable and safe, technique for making this detachable electrical and mechanical connection between the pacemaker device and the connecting end of the pacemaker lead.

Figure 1:
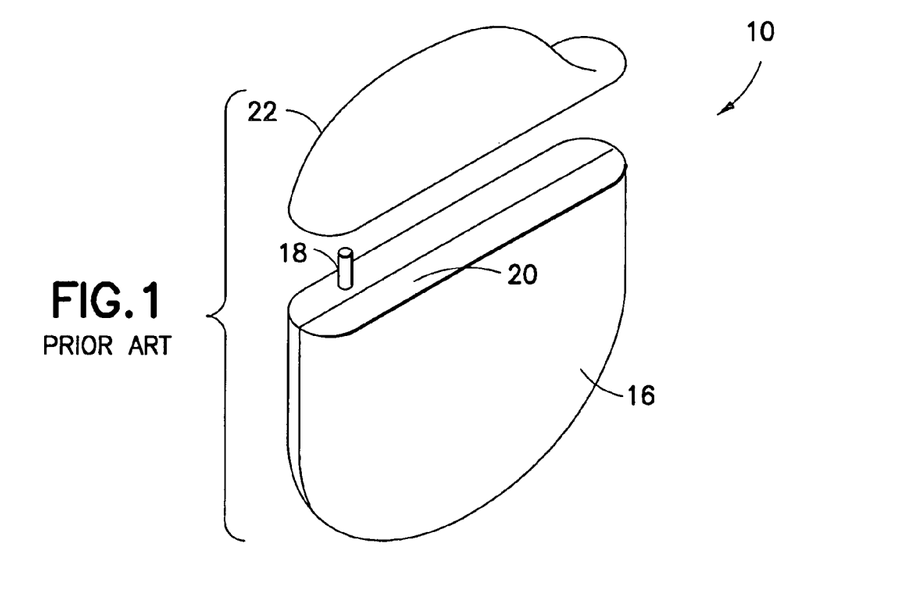
FIG. 1 is an exploded perspective view of a known pacemaker, illustrating a sealed pacemaker housing and its associated header.
Figure 2:
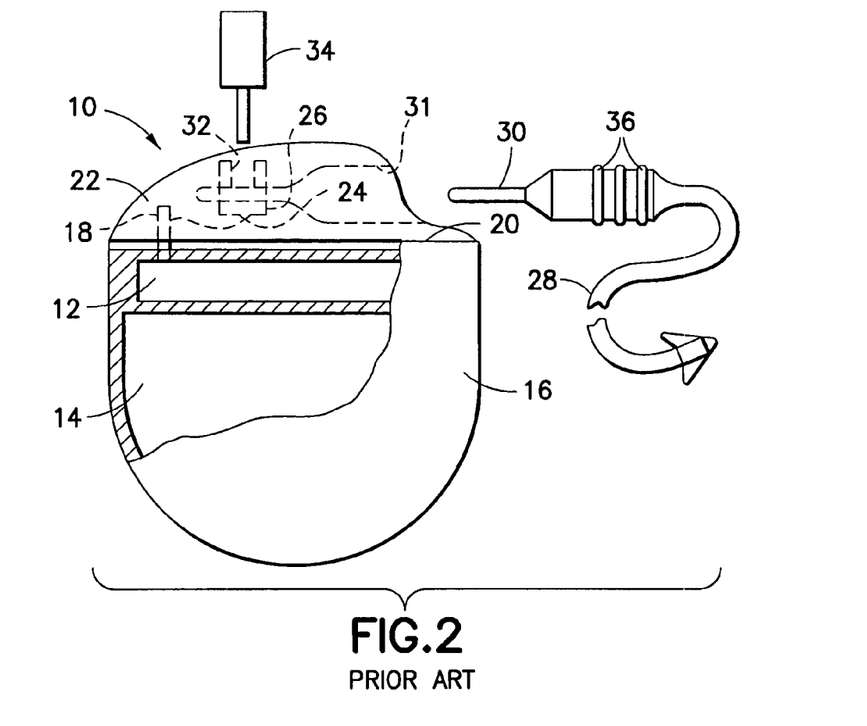
FIG. 2 is a side elevation view, partially cut away and in section, illustrating the assembled relationship between the pacemaker of FIG. 1 and its associated electrical pacemaker lead.

In order to appreciate the advantages of the present invention, it will help first to have a basic understanding of the manner in which the mechanical and electrical connection functions are carried out in known pacemakers. The main components associated with the connection function of known pacemakers are shown in FIGS. 1 and 2. A pacemaker 10 electrically includes a battery 14 that powers electrical circuits 12. The pacemaker electrical circuits 12 and battery 14 are mechanically housed and hermetically sealed in a suitable housing 16. Typically, this housing 16 is shaped to include a flat side or platform 20 to which a suitable epoxy connector 22 can be bonded. At least one feedthrough terminal 18, in electrical contact with the electrical circuits 12, passes through the housing 16 and protrudes out from the platform 20. This feedthrough terminal 18 is electrically isolated from the housing 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 24. A set screw 32 is then securely tightened using a torque wrench 34 to firmly hold the electrode 30 in both mechanical and electrical connection with the connector block 26. A septum (not shown) is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been pushed into the connector 22.

Representative descriptions of many of the features and functions of prior art pacemaker connection systems may be found in U.S. Pat. Nos. 4,934,366 to Truex et al.; 5,383,914 to O'Phelan; Re. 31,990 to Sluetz et al.; and 6,755,694 to Ries et al. Traditionally, as observed in these patents, implantable medical devices have had all leads exiting from the same side of the device. With the advent of HF (heart failure) and other devices with many bores, the lead insertion zone on the header has become cluttered and challenging to determine which lead belongs in which bore. Traditional configurations have all the setscrews and septums grouped in generally the same location, causing the header to have a larger and more intrusive volume. On some medical devices, the high voltage setscrew block (or spring contact) is located far from the feedthrough, necessarily resulting in a long wire with increased resistance that can compromise the lifespan and performance of the medical device.

To counteract this drawback of traditional designs, a multi-directional bore configuration header is hereby proposed which includes two or more lead bores that are open to and align in two or more unique directions, that is, the leads are plugged into the device from two or more unique directions. Other benefits of the multi-directional bore configuration header is to minimize header size, simplify and improve reliability of wire routing, and establish a unique and easily distinguishable bore configuration. The size of a header that houses multiple bores may be significantly reduced by aligning the contained bores in two or more unique directions. This is accomplished by spacing out the setscrew blocks and septums. If the device allows, the bores can be located tip-to-tip reducing vertical height and volume. The internal routing of wires contained within a multi-bore header can be simplified and made more reliable by aligning the bores in multiple directions. A wire's resistance is a function of its length. By shortening the wires, the resistance is reduced thus minimizing battery drain and increasing the life of the battery and device. By aligning the bores in multiple directions, a unique and easily distinguishable bore configuration is established. This simplifies the operating room procedure of determining which bore houses which lead; for example if all IS-4 leads are on the left and all IS-1 leads are on the right. For explanation, IS-4 is a proposed international standard (officially "Active implantable medical devices—four-pole connector system for implantable cardiac rhythm management devices") calls for seals to be placed in the connector cavity and not on the lead connector. The older IS-1 international standard calls for sealing rings on the lead itself, a terminal pin electrode, and a single ring electrode proximally spaced from the terminal pin electrode.

In one known instance, a cardiac monitor includes telemetry to permit cardiac data to be interrogated externally of a patient for obtaining the generated cardiac data indicative of arrhythmic and ischemic episodes. In one embodiment of the monitor, the connector receptacles are disposed in opposing relation permitting conduits to directly extend from the header in opposed relation. However, there is no mention of the particular construction enabling electrical connection to the electronic circuitry within the enclosure for the monitor.

In another known instance, a multi-output connector is disclosed for an implantable stimulator with dual output blocks formed on opposite sides of the device. Again, however, there is no mention of the particular construction enabling electrical connection to the electronic circuitry within the enclosure for the device.

It was in light of the foregoing that the present invention was conceived and has now been reduced to practice.

SUMMARY

An implantable medical device includes a sealed casing enclosing electronic circuitry and a plurality of electrical terminals connected to the electronic circuitry and projecting out of a mounting surface. A header has an undersurface for mounting engagement on the mounting surface of the casing and first and second oppositely directed elongated receptacles, the first receptacle being positioned proximate the electrical terminals. The header also includes at least one conductive connector block having a bore aligned with each of the first and second receptacles for receiving a proximal end portion of a lead extending through the elongated receptacle and carrying at least one electrical terminal and a wire electrically connects each of the connector blocks with an associated electrical terminal, at least the wire from the connector block associated with the first receptacle being of minimal length because of its close proximity to the plurality of electrical terminals.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 4a is a perspective view of a traditional configuration of medical device having a large number of receptacles and associated setscrews and septums grouped at a same location;

FIG. 4b is a front elevation view of the medical device illustrated in FIG. 4a;

DETAILED DESCRIPTION OF THE PREFERRED EMBODIMENT

Figure 3:
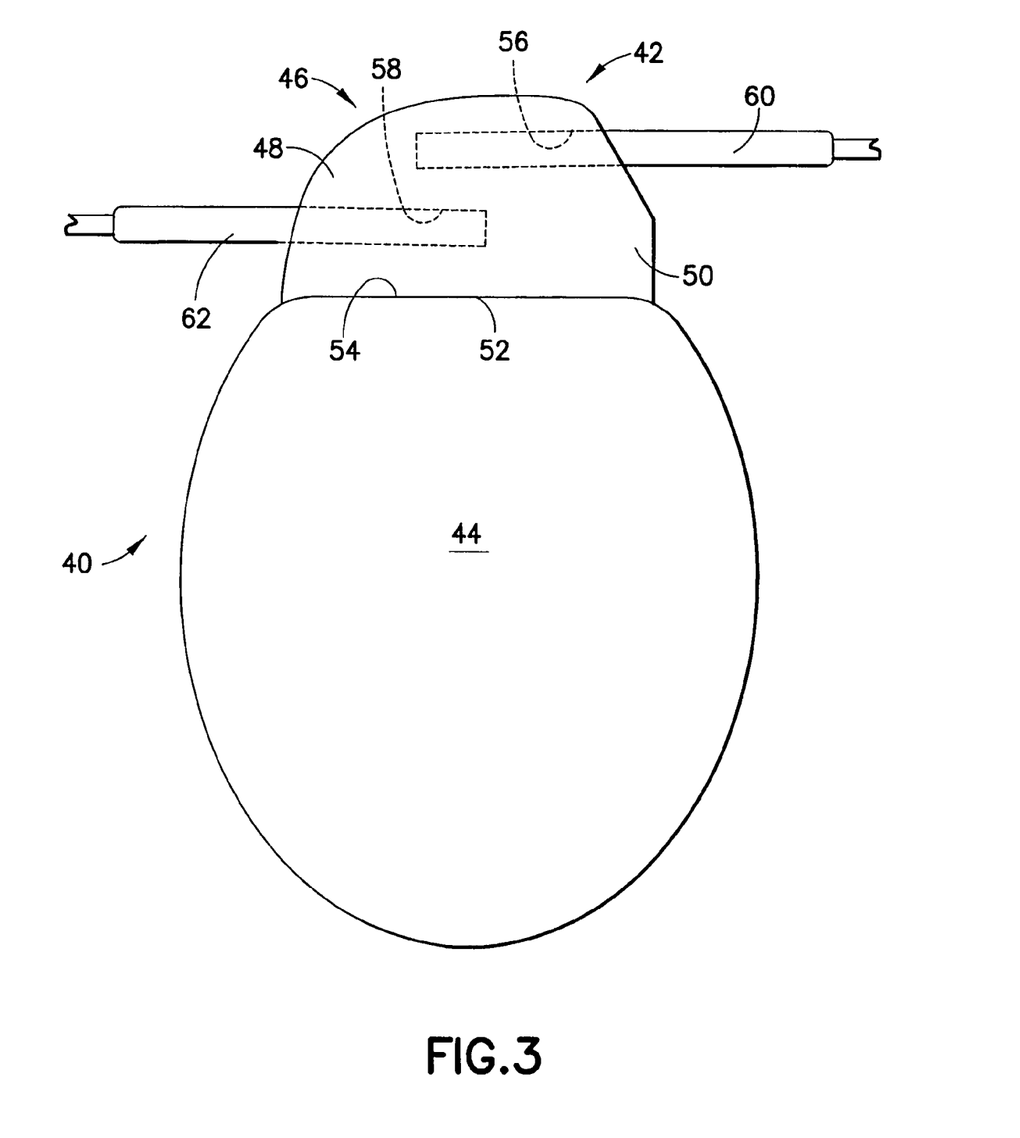
FIG. 3 is a perspective view of a connector assembly for an implantable medical device embodying the present invention.

Referring now to FIG. 3, there is shown a perspective view of an implantable medical device 40 in the form of a pacemaker incorporating features of the present invention. Although the present invention will be described with reference to the embodiments shown in the drawings, it should be understood that the present invention can be embodied in many alternate forms or embodiments. In addition, any suitable size, shape or type of elements or materials compatible with the invention may be used.

The pacemaker 40 In FIG. 3 is seen to include a connector assembly 42 mounted external to a hermetically sealed casing 44 containing electronic circuitry of the nature already illustrated in FIG. 2. The connector assembly 42 includes a header 46 extending between proximal and distal ends 48, 50, respectively, having an undersurface 52 for mounting engagement on a mounting surface 54 of the casing and at least first and second oppositely directed elongated receptacles 56, 58. In the event the implantable medical device 40 is a pacemaker, with which this disclosure is primarily, although not exclusively, concerned, each receptacle 56, 58 is configured to receive the proximal end portions of leads 60, 62 which may be of the pacing and/or sensing variety. Alternatively, in the event the implantable medical device 40 is an implantable cardioverter-defibrillator or ICD, each receptacle 56, 58 may be configured to receive the proximal end portion of a cardioverting and/or defibrillating lead.

Figures 4A, 4B:
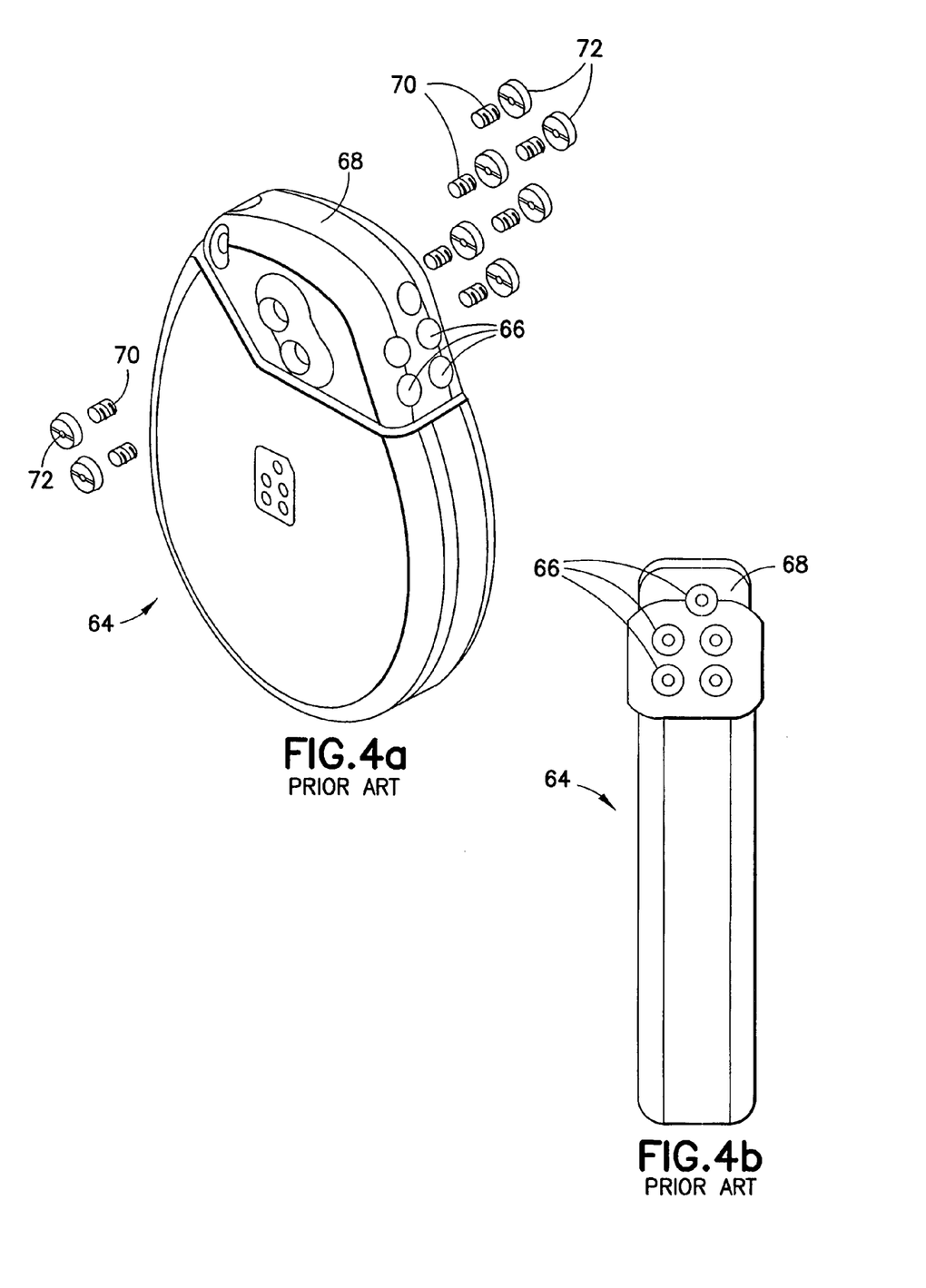

As earlier noted, viewing FIGS. 4a and 4b, traditional configurations of implantable medical devices 64 have had all leads exiting from the same side of the device such that with the advent of HF and other devices with many receptacles 66, the lead insertion zone on a header 68 has become cluttered and challenging to determine which lead belongs in which receptacle. Such traditional configurations have all the setscrews 70 and septums 72 grouped in the same location, causing the header to have a larger and more intrusive volume.

Figure 5A:
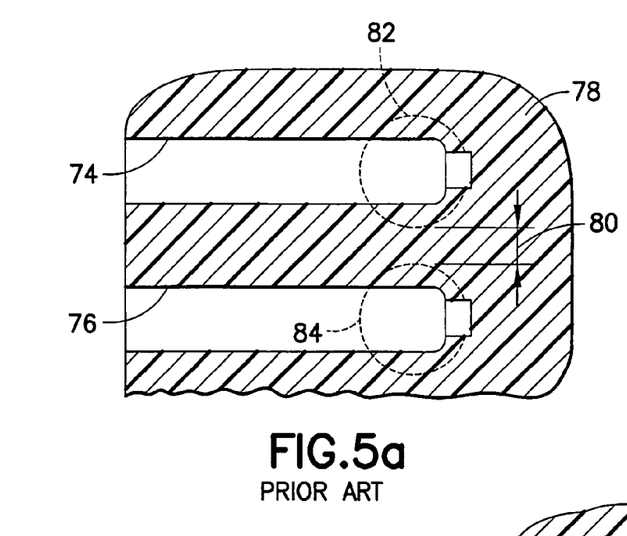
FIG. 5a is a side elevation view, in section, of a known configuration of header.
Figure 5B:
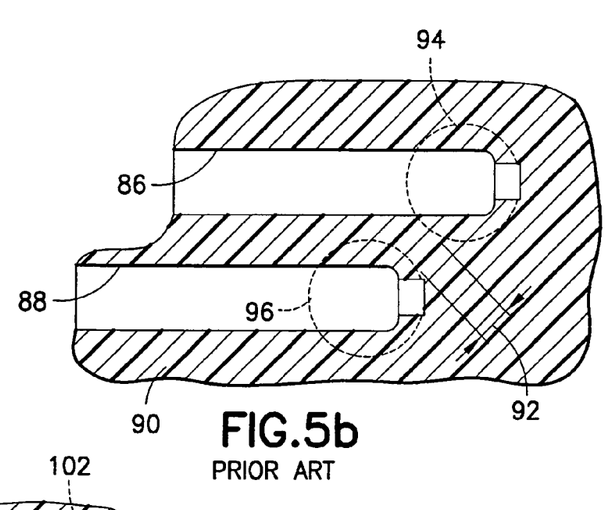
FIG. 5b is a top plan view, in section, of another known configuration of header.
Figure 5C:
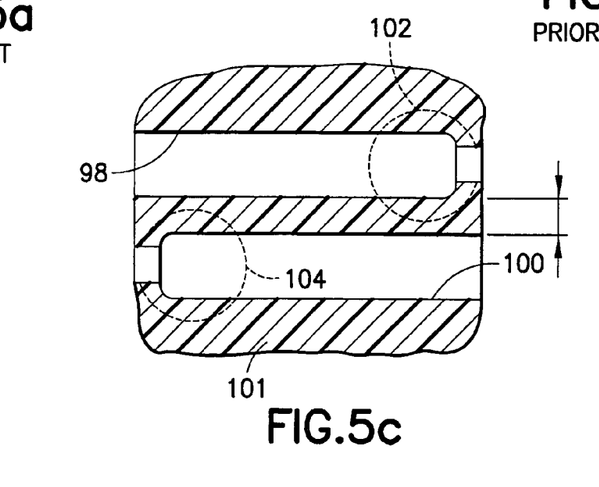
FIG. 5c is a view, in section, either in elevation or in plan, of a configuration of header embodying the present invention.

More specific benefits that will be recognized from the invention can be seen from FIGS. 5a and 5b representative of the prior art and from FIG. 5c representative of the present invention. Thus, in FIG. 5a, in one known instance, vertically spaced receptacles 74, 76 result in an undesirably large height for a header 78 since, for manufacturing purposes, a minimum material allowance 80 is required between adjacent septums 82, 84. Similarly, in FIG. 5b, in another known instance, horizontally spaced receptacles 86, 88 result in an undesirably large width for a header 90 since, for manufacturing purposes, a minimum material allowance 92 is required between adjacent septums 94, 96.

Typical of a benefit achieved by the invention is the arrangement provided in FIG. 5c in which side-by-side receptacles 98, 100 of a header 101, whether vertically spaced or horizontally spaced, result in a minimal vertical or horizontal header dimension. In this instance, among other features, septums 102, 104 are widely spaced allowing the receptacles themselves to be more closely spaced than is permitted in either of the constructions illustrated in FIGS. 4a and 4b.

Figure 6:
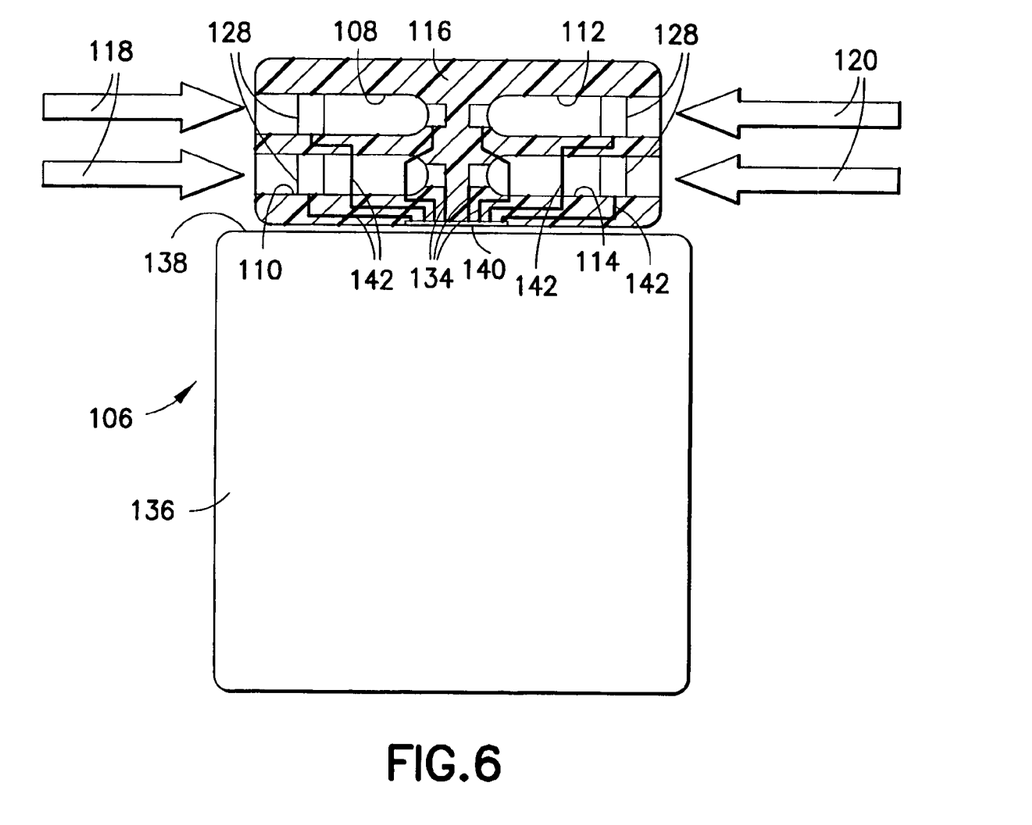
FIG. 6 is a side elevation view, partially cut away and in section, of a configuration of header embodying the present invention.
Figure 7:
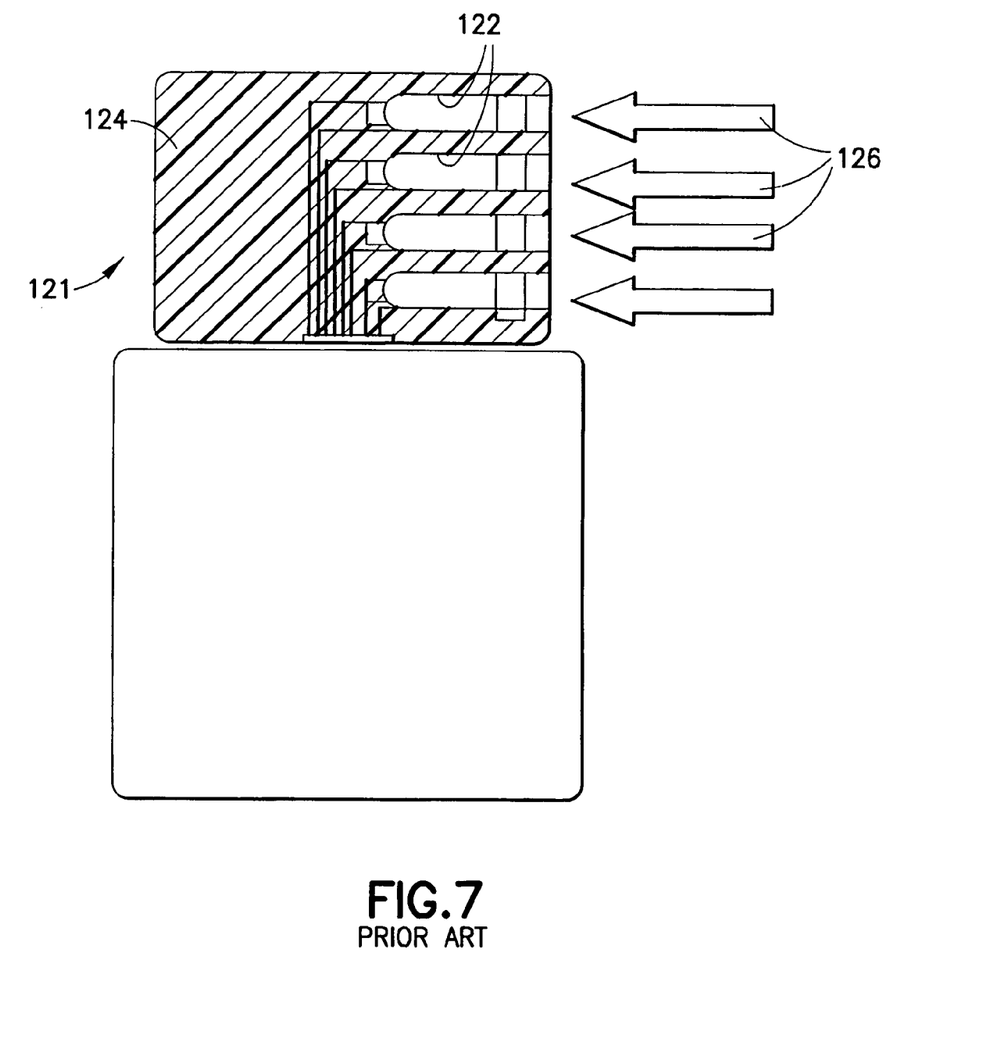
FIG. 7 is a side elevation view, partially cut away and in section, of an undesirable configuration of header which the present invention is intended to correct.

Still more specific benefits that will be recognized from the invention can be seen from FIGS. 6 and 7. As seen in FIG. 6, the present invention promotes the construction of a medical device 106 in which receptacles 108, 110 are positioned tip-to-tip with receptacles 112, 114, respectively, in a header 116.

In this way, leads represented by arrows 118 are introduced into the receptacles 108, 110 from the left as viewed in FIG. 6 and leads represented by arrows 120 are introduced into the receptacles 112, 114 from the right. This contrasts with an alternative, but undesirable, arrangement of a medical device 121, as seen in FIG. 7, in which a plurality of receptacles 122 of a header 124 positioned one above another result in an excessive height of the header with leads represented by arrows 126 shown introduced into the receptacles 122 from the right.

Figure 8:
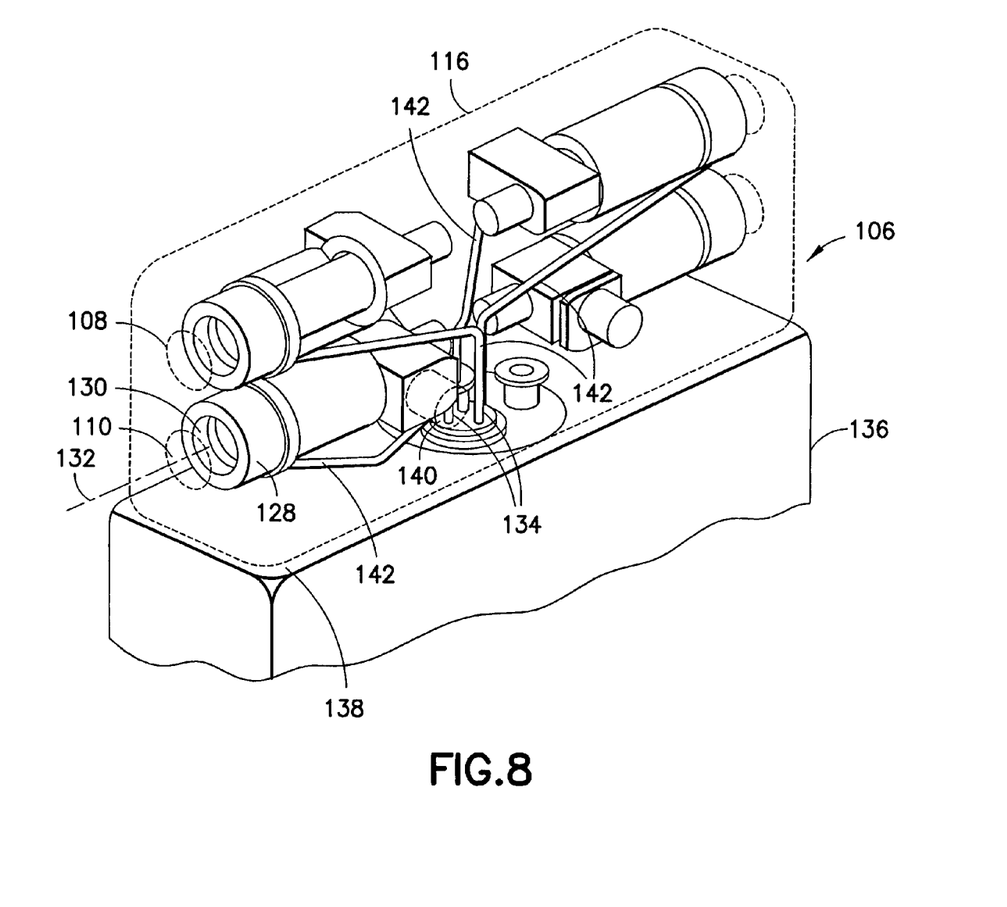
FIG. 8 is a perspective view, partially cut away and in section, of the embodiment illustrated in FIG. 6.

In the FIG. 6 construction of the invention, and turning now, in addition, to FIG. 8, each of the receptacles 108, 110, 112, 114 has at least one associated conductive connector block 128 having a bore 130 aligned with a longitudinal axis 132 of the receptacle. Each receptacle can receive a proximal end portion of a lead 118, 120 (or 60, 62 as seen in FIG. 3) extending through the elongated receptacle and carrying at least one electrical contact in a known manner. A plurality of electrical terminals 134 connected to electronic circuitry (similar to electronic circuitry 12 in FIG. 2) in a casing 136 of the medical device 106 project out of a mounting surface 138 of the casing and, more specifically, out of a feedthrough device 140 integral with the mounting surface and hermetically receiving each of the electrical terminals.

Each receptacle 108, 110, 112, 114 is positioned proximate the electrical terminals 134 and the feedthrough device 140 and a wire 142 electrically connects each of the connector blocks 128 with an associated electrical terminal. With the construction described and illustrated in FIGS. 6a and 7, the wires 142 extending from each of the connector blocks 128 for electrical connection with the electronic circuitry within the casing 136 is of minimal length because of its close proximity to the electrical terminals 134.

For the purposes of the foregoing described medical device 106, the header 116 may be fabricated of a number of possible materials including ceramics, composites, plastics, glass, and metals electrically isolated from the connector blocks 128 and from the wires 142 and encapsulating the connector blocks and the wires.

In the instance illustrated in FIGS. 6 and 8, each of the receptacles 108, 110, 112, 114 has a longitudinal axis 132 and their longitudinal axes are parallel. However, that need not always be the case in order for a medical device to still achieve the benefits of the invention. Turn now to FIG. 9. In this instance, each receptacle 144, 146, and 148 in a header 150 mounted on a casing 152 of a medical device 154 is positioned proximate electrical terminals 156 and their feedthrough device 158. The receptacle 144 with a longitudinal axis 160 is intended to receive a high voltage IS-4 lead while the receptacles 146, 148 with parallel longitudinal axes 162, 164, respectively, are intended to receive low voltage IS-1 leads. For reasons which may include ease of manufacturing and ease of use by the surgeon, the longitudinal axis 160 is angularly disposed relative to longitudinal axes 162, 164.

Figure 9:
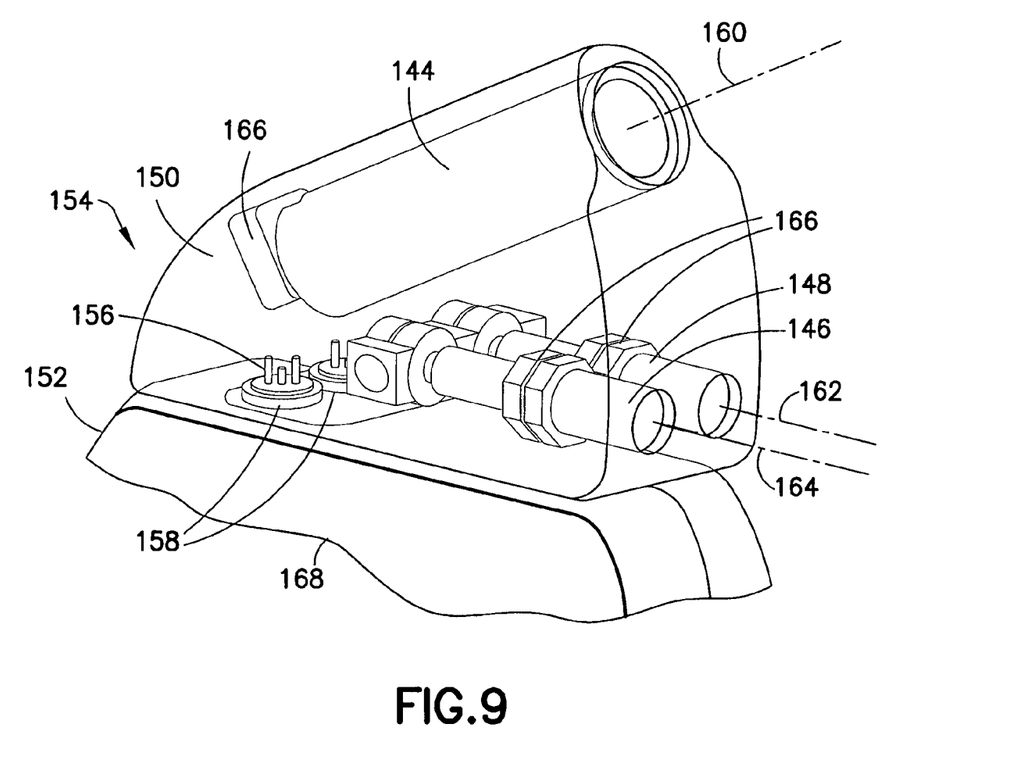
FIG. 9 is a perspective view illustrating another embodiment of the invention.

In FIG. 9, for purposes of simplicity, wires electrically connecting a connector block 166 of the receptacle 144 with an associated electrical terminal 156 and connector blocks 168, 170 of the receptacles 146, 148, respectively, are not shown but would be similar to those illustrated in FIGS. 6 and 8. However, in this instance, also, the wires extending from each of the connector blocks 166, 168, 170 for electrical connection with the electronic circuitry within the casing 152 is of minimal length because of its close proximity to the electrical terminals 156.

In summing up this disclosure, it may be said that a multi-directional bore configuration header is defined as any header that has two or more lead bores that are aligned in two or more unique directions. The procedure for manufacturing a device with this configuration would be nearly identical to one without it. Whether it is a cast header or a pre-molded header, the technology for creating the header would be identical to the traditional configuration. As new medical devices and new headers are designed, the techniques disclosed by the multi-directional bore configuration header of this invention should be used in place of traditional bore configurations.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A connector assembly for an implantable medical device including a casing containing electronic circuitry having a mounting surface and a plurality of electrical terminals of a feedthrough connected to the electronic circuitry and projecting out of the mounting surface, the connector assembly comprising:

a header extending between proximal and distal ends having an undersurface for mounting engagement on the mounting surface of the casing and at least first and second oppositely directed elongated receptacles, the first receptacle and the second receptacle extending along a same longitudinal axis, the plurality of electrical terminals being positioned between the first receptacle and the second receptacle, the header including:

a first conductive connector block having a bore aligned with the longitudinal axis of the first and second receptacles for receiving a proximal end portion of a first lead extending through the first receptacle; and a second conductive connector block having a bore aligned with the longitudinal axis of the first and second receptacles for receiving a proximal end portion of a second lead extending through the second receptacle;

wherein the plurality of electrical terminals of the feedthrough comprise a first electrical terminal and a second electrical terminal;

wherein the first and second conductive connector blocks have first and second interior ends, respectively, that are spaced apart from one another along the longitudinal axis; and first and second wires connecting the first and second interior ends to the first and second electrical terminals, respectively.

2. A connector assembly as set forth in claim 1 wherein each receptacle is configured to receive the proximal end portion of an endocardial pacing and/or sensing lead.

3. A connector assembly as set forth in claim 1 wherein each receptacle is configured to receive the proximal end portion of an endocardial cardioverting and/or defibrillating lead.

4. A connector assembly as set forth in claim 1 wherein the header is of a material selected from the group consisting of ceramics, composites, plastics, glass, and metals electrically isolated from the connector blocks and from the wires and encapsulating the connector blocks and the wires.

5. A connector assembly as set forth in claim 1 including: third and fourth oppositely directed elongated receptacles; wherein the third and fourth receptacle are positioned proximate the plurality of electrical terminals;

wherein the third receptacle is vertically spaced from the first receptacle and the fourth receptacle is vertically spaced from the second receptacle; and wherein the plurality of electrical terminals are positioned between the third receptacle and the fourth receptacle.

6. A connector assembly as set forth in claim 1 including:

wherein the feedthrough is fixed on the mounting surface of the casing hermetically receiving each of the plurality of electrical terminals; and wherein the feedthrough is disposed between the first and second interior ends of the first and second conductive connector blocks.

7. A connector assembly as set forth in claim 1 including:

wherein the first wire is electrically isolated from the second wire.

8. A connector assembly as set forth in claim 1, wherein the first receptacle and the second receptacle are respectively positioned proximate the first wire and the second wire to reduce the length of a subset of a plurality of wires.

9. An implantable medical device comprising:

a sealed casing having a mounting surface;

electronic circuitry enclosed within said casing;

a plurality of electrical terminals of a feedthrough connected to the electronic circuitry and projecting out of the mounting surface;

a header extending between proximal and distal ends having an undersurface for mounting engagement on the mounting surface of the casing and at least first and second oppositely directed elongated receptacles, the first receptacle and the second receptacle extending along a same longitudinal axis, the plurality of electrical terminals being positioned between the first receptacle and the second receptacle, the header including:

a first conductive connector block having a bore aligned with the longitudinal axis of the first and second receptacles for receiving a proximal end portion of a first lead extending through the first receptacle; and a second conductive connector block having a bore aligned with the longitudinal axis of the first and second receptacles for receiving a proximal end portion of a second lead extending through the second receptacle;

wherein the plurality of electrical terminals of the feedthrough comprise a first electrical terminal and a second electrical terminal;

wherein the first and second conductive connector blocks have first and second interior ends, respectively, that are spaced apart from one another along the longitudinal axis; and first and second wires connecting the first and second interior ends to the first and second electrical terminals, respectively, of the feedthrough.

10. An implantable medical device as set forth in claim 9 wherein each receptacle is configured to receive the proximal end portion of an endocardial pacing and/or sensing lead.

11. An implantable medical device as set forth in claim 9 wherein each receptacle is configured to receive the proximal end portion of an endocardial cardioverting and/or defibrillating lead.

12. An implantable medical device as set forth in claim 9 including:

wherein the feedthrough is fixed on the mounting surface of the casing hermetically receiving each of the plurality of electrical terminals; and wherein the feedthrough is disposed between the first and second interior ends of the first and second conductive connector blocks.

13. An implantable medical device as set forth in claim 9 including:

third and fourth oppositely directed elongated receptacles;

wherein the third and fourth receptacle are positioned proximate the plurality of electrical terminals;

wherein the third receptacle is vertically spaced from the first receptacle and the fourth receptacle is vertically spaced from the second receptacle; and wherein the plurality of electrical terminals are positioned between the third receptacle and the fourth receptacle.

14. An implantable medical device as set forth in claim 9 including:

wherein the first wire is electrically isolated from the second wire.

15. An implantable medical device as set forth in claim 9, wherein the first receptacle and the second receptacle are respectively positioned proximate the first wire and the second wire to reduce the length of a subset of a plurality of wires.

* * * * *